(12) United States Patent
Satake et al.

(10) Patent No.: US 9,867,624 B2
(45) Date of Patent: Jan. 16, 2018

(54) ENDOSCOPIC TREATMENT INSTRUMENT

(71) Applicant: OLYMPUS CORPORATION, Hachioji-shi, Tokyo (JP)

(72) Inventors: Motoi Satake, Tokyo (JP); Tomohiro Tsuji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/491,576

(22) Filed: Apr. 19, 2017

(65) Prior Publication Data
US 2017/0215884 A1    Aug. 3, 2017

Related U.S. Application Data

(63) Continuation of application No. PCT/JP2016/064735, filed on May 18, 2016.

(30) Foreign Application Priority Data

May 27, 2015   (JP) .................... 2015-106995

(51) Int. Cl.
*A61B 17/10* (2006.01)
*A61B 17/122* (2006.01)
(Continued)

(52) U.S. Cl.
CPC .......... *A61B 17/122* (2013.01); *A61B 17/083* (2013.01); *A61B 17/10* (2013.01); *A61B 2017/00323* (2013.01)

(58) Field of Classification Search
CPC .......... A61B 17/122; A61B 2017/1225; A61B 17/083; A61B 17/10; A61B 2017/00323
(Continued)

(56) References Cited

U.S. PATENT DOCUMENTS 3,958,576 A * 5/1976 Komiya ............... A61B 17/083
                                                        24/456
5,156,609 A * 10/1992 Nakao ................ A61B 17/0682
                                                        227/179.1
(Continued)

FOREIGN PATENT DOCUMENTS

JP      2004-073646 A    3/2004
WO  2013/179106 A1   12/2013

OTHER PUBLICATIONS

Aug. 9, 2016 International Search Report issued in International Patent Application No. PCT/JP2016/064735.

*Primary Examiner* — Eric Rosen
*Assistant Examiner* — Son Dang
(74) *Attorney, Agent, or Firm* — Oliff PLC

(57) ABSTRACT

An endoscopic treatment instrument includes a pressing tube with an insertion lumen; a clip main body that has a first arm being inserted into the insertion lumen; a second arm fixed to the pressing tube; and an operation wire connected to the clip main body to move it with respect to the pressing tube, wherein the first arm approaches the second arm while being moved to a proximal end side of the pressing tube, in an initial state before the clip main body is pulled by the operation wire, a position of a distal end of the first arm is more distal than a position of a distal end of the second arm, and the distal end of the first arm is approaches the distal end portion of the second arm when the clip main body is pulled to the proximal end side of the pressing tube.

4 Claims, 15 Drawing Sheets

(51) Int. Cl.
*A61B 17/08* (2006.01)
*A61B 17/00* (2006.01)

(58) Field of Classification Search
USPC .................................................. 606/205, 207
See application file for complete search history.

(56) References Cited

U.S. PATENT DOCUMENTS

| | | | | | |
|---|---|---|---|---|---|
| 5,766,189 | A * | 6/1998 | Matsuno | | A61B 17/122 606/139 |
| 5,989,277 | A * | 11/1999 | LeMaire, III | | A61B 17/1608 606/170 |
| 6,090,129 | A * | 7/2000 | Ouchi | | A61B 17/221 606/113 |
| 6,679,894 | B2 * | 1/2004 | Damarati | | A61B 17/122 29/243.56 |
| 7,108,699 | B2 * | 9/2006 | Kobayashi | | A61B 17/122 606/142 |
| 7,223,271 | B2 * | 5/2007 | Muramatsu | | A61B 17/1227 606/139 |
| 7,338,503 | B2 * | 3/2008 | Rosenberg | | A61B 17/12 606/142 |
| 7,494,461 | B2 * | 2/2009 | Wells | | A61B 17/122 600/104 |
| 7,736,374 | B2 * | 6/2010 | Vaughan | | A61B 17/0401 606/144 |
| 7,824,407 | B2 * | 11/2010 | Yamamoto | | A61B 18/1445 606/46 |
| 8,062,310 | B2 * | 11/2011 | Shibata | | A61B 17/1285 227/175.1 |
| 8,080,021 | B2 * | 12/2011 | Griego | | A61B 17/068 29/812 |
| 8,241,307 | B2 * | 8/2012 | Benson | | A61B 17/0469 606/148 |
| 8,245,377 | B2 * | 8/2012 | Ormachea | | B68G 7/05 269/37 |
| 8,672,952 | B2 * | 3/2014 | Suzuki | | A61B 17/00234 606/142 |
| 8,900,253 | B2 * | 12/2014 | Aranyi | | A61B 17/122 606/142 |
| 8,900,254 | B2 * | 12/2014 | Kobayashi | | A61B 17/1227 606/139 |
| 8,979,891 | B2 * | 3/2015 | McLawhorn | | A61B 17/08 606/142 |
| 9,072,517 | B2 * | 7/2015 | Qadeer | | A61B 17/0682 |
| 9,072,520 | B2 * | 7/2015 | Terada | | A61B 17/1222 |
| 9,492,176 | B2 * | 11/2016 | Zhu | | A61B 17/122 |
| 2002/0045909 | A1 * | 4/2002 | Kimura | | A61B 17/083 606/151 |
| 2003/0069592 | A1 * | 4/2003 | Adams | | A61B 17/122 606/142 |
| 2004/0176784 | A1 * | 9/2004 | Okada | | A61B 17/1285 606/142 |
| 2005/0107809 | A1 * | 5/2005 | Litscher | | A61B 17/122 606/142 |
| 2007/0112359 | A1 * | 5/2007 | Kimura | | A61B 17/122 606/142 |
| 2007/0250112 | A1 * | 10/2007 | Ravikumar | | A61B 17/00234 606/205 |
| 2008/0027467 | A1 * | 1/2008 | Satake | | A61B 17/1285 606/143 |
| 2008/0140089 | A1 * | 6/2008 | Kogiso | | A61B 17/122 606/142 |
| 2008/0306491 | A1 * | 12/2008 | Cohen | | A61B 17/122 606/142 |
| 2009/0326558 | A1 * | 12/2009 | Cui | | A61B 17/1227 606/143 |
| 2010/0036396 | A1 * | 2/2010 | Iida | | A61B 17/1285 606/143 |
| 2010/0152753 | A1 * | 6/2010 | Menn | | A61B 17/122 606/158 |
| 2010/0274268 | A1 * | 10/2010 | Singh | | A61B 17/122 606/157 |
| 2013/0123818 | A1 * | 5/2013 | Li | | A61B 17/122 606/157 |
| 2014/0180014 | A1 * | 6/2014 | Ransden | | A61B 17/0401 600/204 |
| 2015/0190136 | A1 * | 7/2015 | Cohen | | A61B 17/122 606/143 |
| 2017/0215886 | A1 * | 8/2017 | Muyari | | A61B 17/1285 606/139 |

* cited by examiner

ENDOSCOPIC TREATMENT INSTRUMENT

This application is a continuation application based on a PCT International Application No. PCT/JP2016/064735, filed on May 18, 2016, whose priority is claimed on Japanese Patent Application No. 2015-106995, filed on May 27, 2015. The contents of both of the PCT International Application and the Japanese Patent Application are incorporated herein by reference.

BACKGROUND OF THE INVENTION

Field of the Invention

The present invention relates to an endoscopic treatment instrument used for ligating a tissue by being inserted into a body.

Description of Related Art

In the related art, an endoscopic clip device is inserted into a body by using an endoscope device to ligate a treatment target area as a treatment instrument for closing a wound occurred in a living body tissue and performing hemostasis treatment. For example, in Japanese Unexamined Patent Application, First Publication No. 2004-73646, it is disclosed that a ligation device has a clip unit with a plurality of arms that are coupled to an operation wire and the clip unit is displaced by retracting the clip unit into a tube member fixed to a distal end of a coil sheath such that distal ends of each arm approaches each other to close a defective area of a mucous membrane as the treatment target area. According to the ligation device disclosed in Japanese Unexamined Patent Application, First Publication No. 2004-73646, after the distal ends of the arms are closed, coupling of the operation wire and the arms, and connection of the tube member and the coil sheath are released. As a result, the clip unit is spaced from the ligation device and is placed on the tissue (mucous membrane).

SUMMARY OF THE INVENTION

According to a first aspect of the present invention, an endoscopic treatment instrument includes a pressing tube that has an insertion lumen; a clip main body that has a first arm, the first arm being inserted into the insertion lumen such that the first arm protrudes from a distal end of the pressing tube; a second arm that is fixed to the pressing tube to protrude to a distal end side of the pressing tube; and an operation wire that is connected to the clip main body and configured to advance and retract the clip main body with respect to the pressing tube. The first arm approaches the second arm while being moved to a proximal end side of the pressing tube by being pulled by the operation wire. In an initial state before the clip main body is pulled by the operation wire, a position of a distal end of the first arm in a longitudinal axis direction of the pressing tube is more distal than a position of a distal end of the second arm. The distal end of the first arm is configured to approach the distal end portion of the second arm when the clip main body is pulled to the proximal end side of the pressing tube.

According to a second aspect of the present invention, in the endoscopic treatment instrument according to the above-described first aspect, the first arm may be disposed so as to incline with respect to a longitudinal axis of the pressing tube when the first arm protrudes from the distal end portion of the pressing tube, and the second arm may be fixed to the pressing tube at an angle which is substantially parallel to the longitudinal axis.

According to a third aspect of the present invention, in the endoscopic treatment instrument according to the above-described first aspect or second aspect, the first arm may be configured to be elastically deformable and have a shape inclined in a direction in which the distal end portion of the first arm is spaced from the longitudinal axis of the pressing tube, in a state where the first arm protrudes from the distal end portion of the pressing tube, and the first arm may be pressed by the pressing tube to be elastically deformed when the clip main body is pulled to the proximal end side of the pressing tube.

According to a fourth aspect of the present invention, in the endoscopic treatment instrument according to the above-described second aspect, the clip main body may have a connection portion to be connected to the operation wire on the proximal end side of the clip main body, and a connection between the operation wire and the clip main body may be released as the connection portion protrudes from the proximal end of the pressing tube, while the clip main body is pulled toward the proximal end side of the pressing tube.

DETAILED DESCRIPTION OF THE INVENTION

First Embodiment

Figure 1:
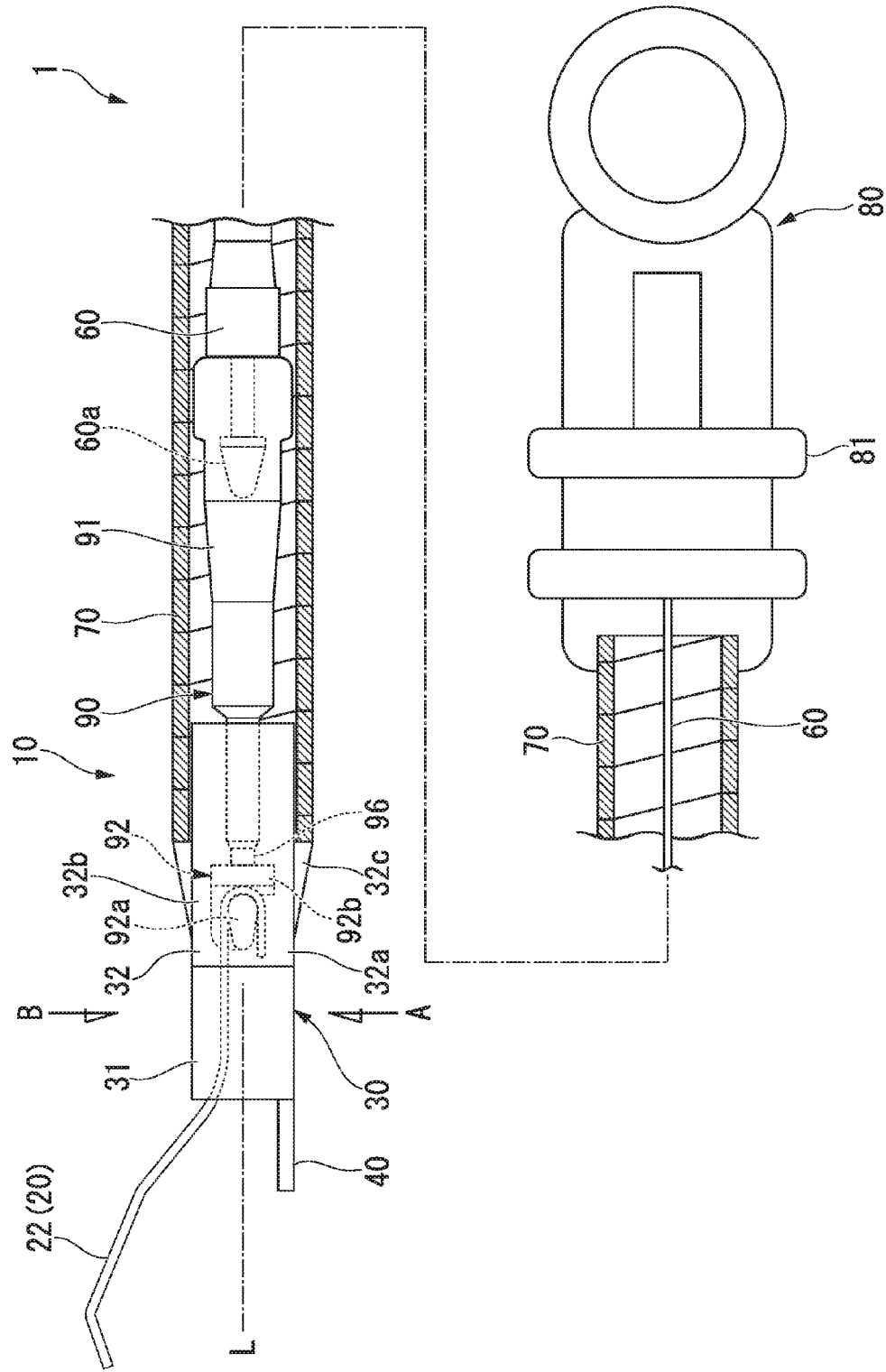
FIG. 1 is an overall view showing an endoscopic treatment instrument according to a first embodiment of the present invention.
Figure 2:
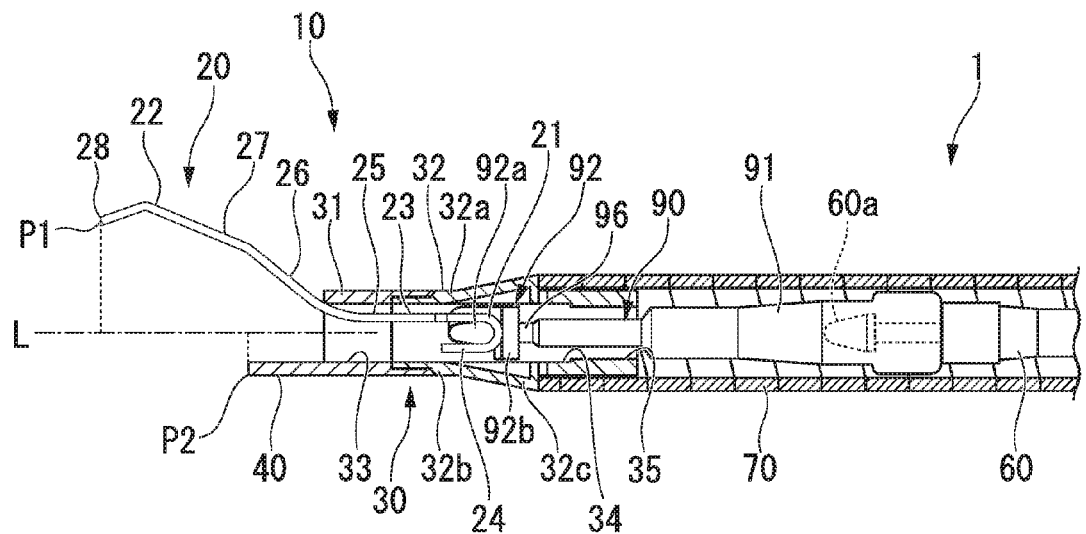
FIG. 2 is a partial sectional view showing a distal end portion of the endoscopic treatment instrument according to the first embodiment of the present invention.
Figure 3:
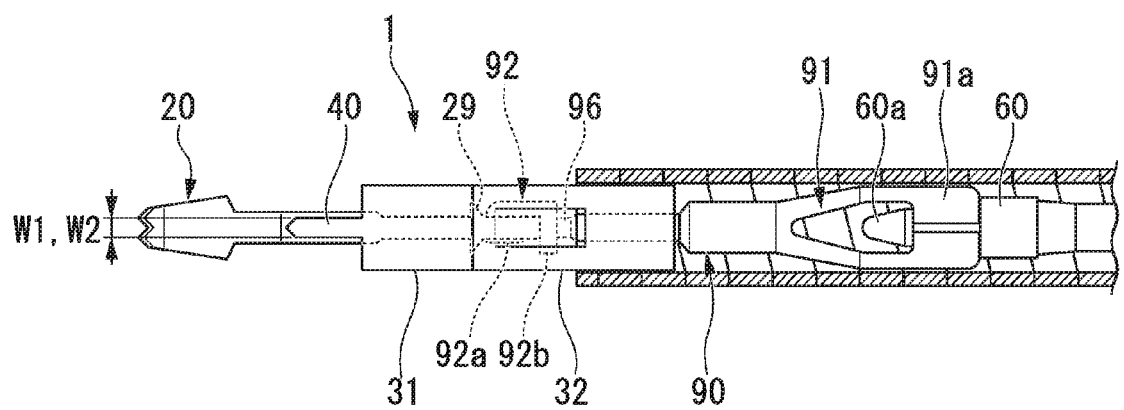
FIG. 3 is a view showing the distal end portion of the endoscopic treatment instrument according to the first embodiment of the present invention.
Figure 4:
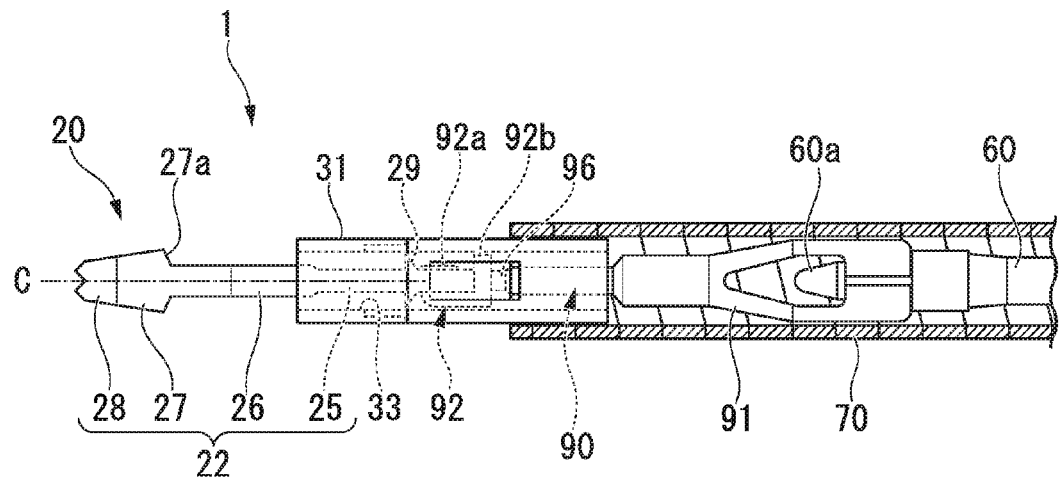
FIG. 4 is a view showing the distal end portion of the endoscopic treatment instrument according to the first embodiment of the present invention.

An endoscopic treatment instrument (hereinafter, simply referred to as a "treatment instrument") according to a first embodiment of the present invention will be described. FIG. 1 is an overall view showing a treatment instrument 1 according to the present embodiment. FIG. 2 is a sectional view showing a distal end portion of the treatment instrument 1. FIG. 3 is a view when the distal end portion of the treatment instrument 1 is viewed in a direction indicated by an arrow A in FIG. 1. FIG. 4 is a view when the distal end portion of the treatment instrument is viewed in a direction indicated by an arrow B in FIG. 1. In FIGS. 2 to 5B and FIGS. 7 to 11, a sheath 70 is shown using a cross section on a plane passing through a central axis of a pressing tube 30.

As shown in FIGS. 1 and 2, the treatment instrument 1 according to the present embodiment has a clip unit 10, an operation wire 60, and the sheath 70. The clip unit 10 includes a clip main body 20, the pressing tube 30, and a second arm 40, and is mounted at a distal end of the sheath 70 into which the operation wire 60 is inserted. The clip main body 20, the second arm 40, the operation wire 60, and the sheath 70 are disposed along a central axis (longitudinal axis) L in a longitudinal direction of the pressing tube 30.

As shown in FIGS. 2 and 3, for example, the clip main body 20 is formed by performing a bending process on a thin and long metal plate. For example, a material of the clip main body 20 includes stainless steel, a cobalt chromium alloy, or a titanium alloy. The clip main body 20 has a bending portion 21 disposed on a proximal end side, and a first arm 22 disposed so as to extend to a distal end side from the bending portion 21.

The bending portion 21 is formed in an arc shape by bending the clip main body 20 in a plate thickness direction. Both end portions of the bending portion 21 extend to the distal end side so as to be substantially parallel to each other, thereby forming a first extension portion 23 and a second extension portion 24. The first arm 22 extending in a distal end direction is disposed on the distal end side of the first extension portion 23. The distal end of the second extension portion 24 is disposed in a second tubular portion 32 that is described later. According to the present embodiment, in the clip main body 20, a single stainless steel plate is subjected to the bending process to form the bending portion 21, the first extension portion 23, the second extension portion 24, and the first arm 22.

The first arm 22 is disposed so as to extend from the distal end of the first extension portion 23 to the distal end portion of the clip main body 20. The distal end of the first arm 22 protrudes more distally than the distal end of the second extension portion 24. That is, a portion close to one end portion in the longitudinal direction of the thin and long stainless steel plate is subjected to the bending process to form the bending portion 21. Hereinafter, a surface located on an inner side of the bending portion 21 in the clip main body 20 is referred to as an inner surface, and a surface located on an outer side of the bending portion 21 is referred to as an outer surface.

Figure 5A:
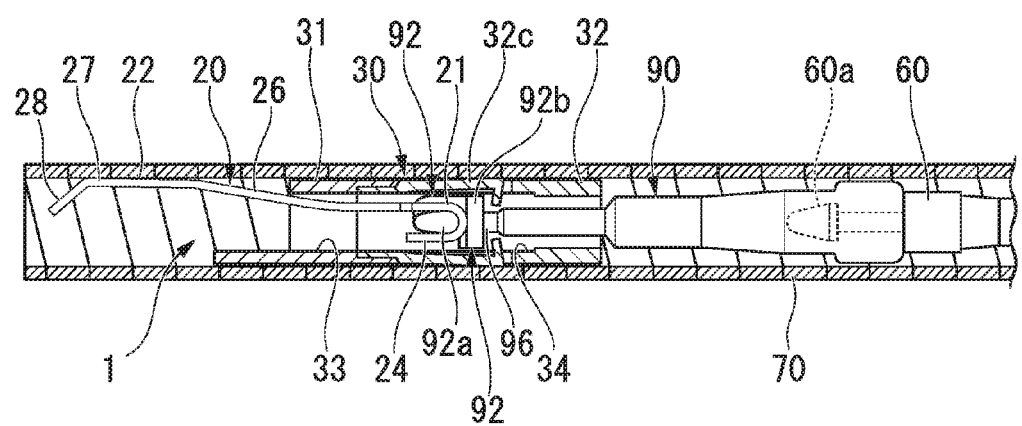
FIG. 5A is a partial sectional view showing the distal end portion of the endoscopic treatment instrument according to the first embodiment of the present invention.
Figure 5B:
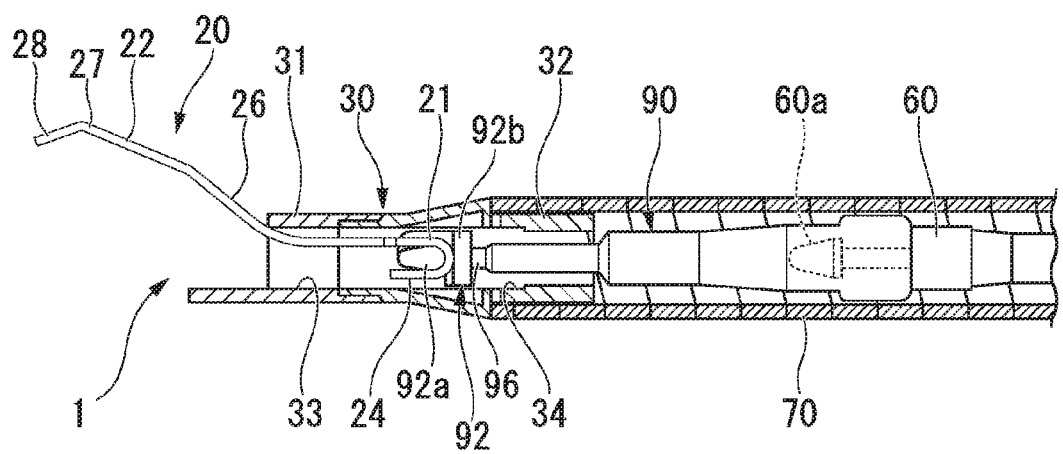
FIG. 5B is a partial sectional view showing the distal end portion of the endoscopic treatment instrument according to the first embodiment of the present invention.

The first arm 22 has a first portion 25, a second portion 26, and a third portion 27. The first portion 25 is formed so as to extend to the distal end along an extending direction of the first extension portion 23. The second portion 26 is subjected to the bending process so as to be bent to the outer surface side from the first portion 25. As shown in FIGS. 5A and 5B, the third portion 27 is subjected to the bending process so as to be bent to the inner surface side in the distal end portion of the second portion 26 and the third portion 27 is disposed to have a wider plate width than that of the second portion 26.

A serrated projection 29 which projects in such a way that both sides of the clip main body 20 are widened in a plate width direction is formed between the first extension portion 23 and the first portion 25. The plate width in the projection 29 is set to a width substantially the same as or slightly wider than an opening width of a third insertion lumen 35. As shown in FIG. 4, in the serrated shape of the projection 29, the distal end side extends in a direction orthogonal to a center line C in the plate width direction of the clip main body 20, and has a shape whose proximal end side inclines. The serrated projection 29 may also be similarly disposed in the second extension portion 24.

As shown in FIG. 2, the second portion 26 is bent to the outer surface side, and the second portion 26 is bent like a bow in a separating direction in which the second portion inclines with respect to a longitudinal axis L of the pressing tube 30 in a state where the second portion 26 protrudes from the pressing tube 30.

The first arm 22 further has a fourth portion (distal end portion) 28 which is folded to the inner surface side in the distal end portion of the third portion 27. The fourth portion 28 is bent in the distal end of the third portion 27, and inclines with respect to the inner surface side. As shown in FIG. 4, in the fourth portion 28, the plate width is gradually narrowed from the proximal end side toward the distal end side, and the distal end portion is formed in a serrated shape.

The plate width of the clip main body 20 is equal in the bending portion 21, the first extension portion 23, the second extension portion 24, and the first portion 25. The third portion 27 is further widened on the proximal end side compared to the second portion 26, and has a wider plate width than an opening width of a first insertion lumen 33 of a first tubular portion 31 of the pressing tube 30 that is described later. The third portion 27 is formed so that the plate width is gradually narrowed toward the distal end side. According to the present embodiment, the second portion 26 has the wider plate width than that of the first portion 25, and the second portion 26 may have substantially the same plate width than that of the first portion 25.

The first arm 22 is formed to the above-described shape by being bent in advance, and the first arm 22 is formed to be capable of elastically deforming if an external force is applied and capable of restoring to the above-described bent shape in a state where the external force is not applied thereto. The clip main body 20 is inserted into the first insertion lumen 33 so that the first arm 22 protrudes from the distal end of the pressing tube 30. The bending portion 21 of the clip main body 20 is engaged to a coupling member that is described later.

Figure 6:
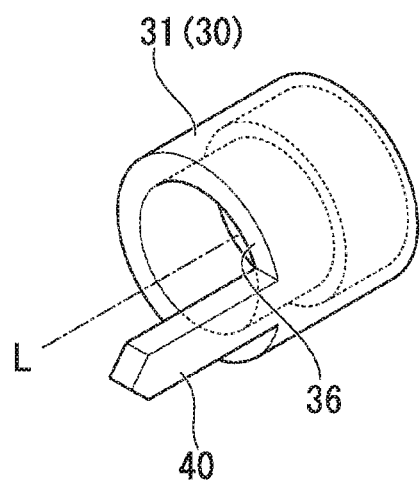
FIG. 6 is a perspective view showing a tubular portion according to the first embodiment of the present invention.

The pressing tube 30 has the first tubular portion 31 disposed on the distal end side, and the second tubular portion 32 disposed on the proximal end side. Insertion lumens 33 and 34 are formed therein. FIG. 6 is a perspective view of the first tubular portion 31. The first tubular portion 31 is a substantially tubular member having a smaller diameter than an opening diameter of the lumen of the sheath 70.

In the second tubular portion 32, the second insertion lumen 34 is formed on the distal end side, and the third insertion lumen 35 is formed on the proximal end side. Both of these communicate with each other from the distal end to the proximal end. The second insertion lumen 34 and the third insertion lumen 35 have a dimension which enables a distal end portion of a coupling member 90 to move forward or rearward.

The second tubular portion 32 has a main body 32a and protruding portions 32c. The main body 32a has a slightly smaller outer diameter than the opening diameter of the lumen of the sheath 70. The protruding portions 32c are disposed in an outer peripheral surface 32b of the main body 32a. As shown in FIGS. 1 and 2, the protruding portions 32c are disposed at two locations on the outer peripheral surface 32b of the second tubular portion 32 so that a triangular flat plate protrudes outward in a radial direction. The two protruding portions 32c are separately disposed at an interval of 180 degrees in a circumferential direction of the second tubular portion 32. The protruding portions 32c are disposed so as to be elastically deformable inward of the second tubular portion 32 if a pressing force is applied thereto from the outside in the radial direction of the second tubular portion 32.

In the pressing tube 30, the proximal end portion of the first tubular portion 31 is fitted and fixed to the distal end portion of the second tubular portion 32. The first insertion lumen 33 formed in the first tubular portion 31 and the second insertion lumen 34 formed inside the second tubular portion 32 have substantially the same opening diameter, and communicate with each other. The clip main body 20 is advanceably and retractably inserted into the first insertion lumen 33 and the second insertion lumen 34. For example, the pressing tube 30 is manufactured by using a metal material such as stainless steel, a titanium alloy (Ti-6AL-4V), and a cobalt chromium alloy, or a rigid resin material having moderate elasticity such as polyphthalamide (PPA) and polyamide (PA).

The pressing tube 30 is disposed to be advanceable and retractable with respect to the sheath 70, and attachable to or detachable from the sheath 70. An outer peripheral diameter of the proximal end portion of the second tubular portion 32 is formed to be slightly smaller than the opening diameter of the lumen of the sheath 70. As shown in FIG. 5A, the pressing tube 30 can be accommodated inside the sheath 70 in such a way that the protruding portion 32c is pressed inward of the second tubular portion 32. As shown in FIG. 2, when the pressing tube 30 protrudes from the distal end of the sheath 70, the pressing tube 30 is inserted into the sheath 70 in a state where the outer peripheral surface of the proximal end portion of the second tubular portion 32 moves close to an inner wall of the lumen of the sheath 70, and the pressing tube 30 is connected to the sheath 70 in a state where each proximal end surface of the two protruding portions 32c is in contact with the distal end portion of the sheath 70. In a state where the pressing tube 30 is connected to the sheath 70, the proximal end surface of the protruding portion is in contact with the distal end portion of the sheath 70 such that the pressing tube 30 is connected to the sheath 70 so as to be immovable relative to the proximal end side.

As shown in FIG. 6, the second arm 40 protrudes from and fixed to the distal end portion of the pressing tube 30 such that the second arm 40 extends more distally than the distal end side of the pressing tube 30. The second arm 40 protrudes from one portion of an opening edge 36 of the distal end of the first tubular portion 31, and extends along a direction of the longitudinal axis L of the first tubular portion 31. The second arm 40 according to the present embodiment is formed integrally with the first tubular portion 31.

In a state where the first arm 22 protrudes to the distal end side of the first tubular portion 31 (initial state), as shown in FIG. 2, a position P1 of the fourth portion 28 in the direction of the longitudinal axis L of the pressing tube 30 is located more distal than a position P2 of a distal end portion 41 of the second arm 40. That is, a protruding length of the first arm 22 from the opening edge 36 (distal end portion of the pressing tube) of the first tubular portion 31 is longer than a protruding length of the second arm 40 from the opening edge 36 of the first tubular portion 31. On the other hand, a configuration is adopted in which the first arm 22 is elastically deformed after coming into contact with the pressing tube 30 such that the first arm 22 faces the second arm 40, when the clip main body 20 is pulled to the proximal end side of the pressing tube 30. As shown in FIG. 3, a width W2 of the second arm 40 has substantially the same dimension as a plate width W1 of grasping portion of the clip main body 20. The inner surfaces of the second arm 40 and the first arm 22 are disposed at mutually facing positions.

The clip main body 20 and the operation wire 60 are detachably connected to each other via the coupling member 90. The coupling member 90 is formed of a metal or resin material. The coupling member 90 is disposed at the distal end of the operation wire 60 inserted into the sheath 70, and connects the operation wire 60 and the clip main body 20 to each other. The coupling member 90 has a coupler 91, an engaging portion 92, and a small diameter portion 96, sequentially from the proximal end side. The coupling member 90 is connected to the operation wire 60 by the coupler 91, and is connected to the clip main body 20 by the engaging portion 92. The coupling member 90 has a pair of grasping clips 91a on the proximal end side of the coupler 91. As shown in FIG. 2, the engaging portion 92 has a substantially L-shaped base 92b disposed on the distal end side of the small diameter portion 96, and an engaging projection portion 92a disposed so as to protrude from the base 92b in a direction orthogonal to the longitudinal axis L. The engaging projection portion 92a has a shape extending along a shape on the inner surface side of the bending portion 21 of the clip main body 20.

The sheath 70 is a coil sheath whose wire is densely wound in the direction of the longitudinal axis L. The sheath 70 is configured to be flexible and have a sturdy structure resistant to a compressive force in the direction of the longitudinal axis L. As shown in FIG. 1, an operation unit 80 is connected to the proximal end portion of the sheath 70. The operation wire 60 is inserted into the sheath 70, and the proximal end portion of the operation wire 60 is connected to a slider 81 of the operation unit 80. An operator operates the slider 81 of the operation unit 80 to slide such that the operation wire 60 advances or retracts with respect to the sheath 70.

Next, a connection structure among the clip main body 20, the pressing tube 30, the coupling member 90, and the operation wire 60 will be described. The operation wire 60 inserted into the sheath 70 has an arrowhead hook 60a in the distal end of the operation wire 60. The arrowhead hook 60a and a grasping clip 91a engage with each other, thereby connecting the coupling member 90 to the operation wire 60.

The clip main body 20 is engaged by the engaging portion 92 of the coupling member 90 inside the insertion lumen of the pressing tube 30. Specifically, the engaging portion 92 and the clip main body 20 engage with each other by inserting the bending portion 21 through the insertion lumens 33, 34, and 35 that are disposed between the engaging projection portion 92a and the base 92b. According to the above-described configuration, the clip main body 20 is engaged by the coupling member 90 in a state where the clip main body 20 is inserted into the pressing tube 30, and the clip main body 20 is disposed to be advanceable and retractable with respect to the first insertion lumen 33 and the second insertion lumen 34 of the pressing tube 30 together with the advancement and retraction of the operation wire 60 with respect to the sheath 70.

The treatment instrument 1 is assembled in the following procedure.

The clip unit 10 is installed inside a cartridge (not shown). Once the cartridge is inserted and pressed into the lumen of the sheath 70, the grasping clip 91a and the arrowhead hook 60a engage with each other in the proximal end portion of the cartridge. In this state, if the cartridge is detached therefrom, the clip unit 10 is brought into a state where the clip unit 10 is accommodated in the distal end portion of the sheath 70, as shown in FIG. 5A. At this time, the first arm 22 accommodated inside the sheath 70 is elastically deformed in a direction close to the longitudinal axis L. As shown in FIGS. 2 and 3, a position of the fourth portion 28 (distal end of the first arm) in the direction of the longitudinal axis L of the pressing tube 30 is located on the distal end side from a position of the distal end portion 41 of the second arm 40. The protruding portion 32c is pressed against the inner wall of the lumen of the sheath 70, and is elastically deformed to the inner side (second insertion lumen 34 side) of the second tubular portion 32.

In this state, the treatment instrument 1 is in an initial state where the treatment instrument 1 can be used for surgical treatment. The sheath 70 into which the treatment instrument 1 is inserted is inserted into an endoscope insertion portion of an endoscope device that is not shown, and the treatment instrument 1 is used for ligation treatment.

Figure 7:
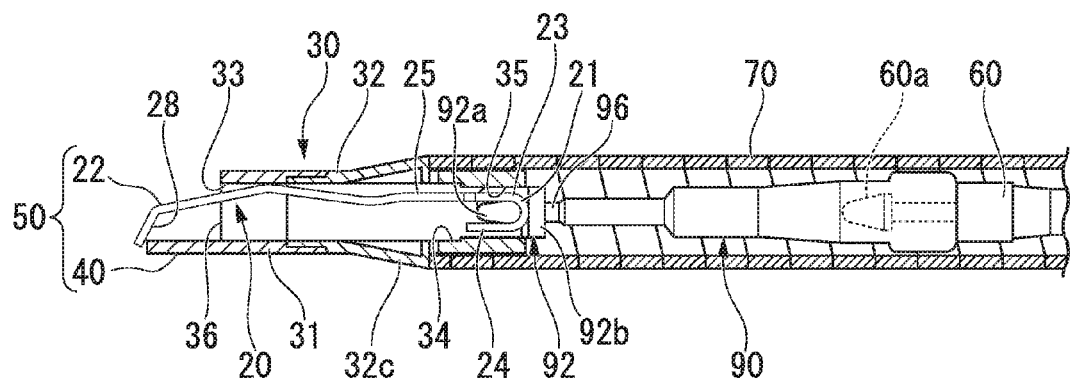
FIG. 7 is a partial sectional view showing the distal end portion of the endoscopic treatment instrument according to the first embodiment of the present invention.
Figure 8:
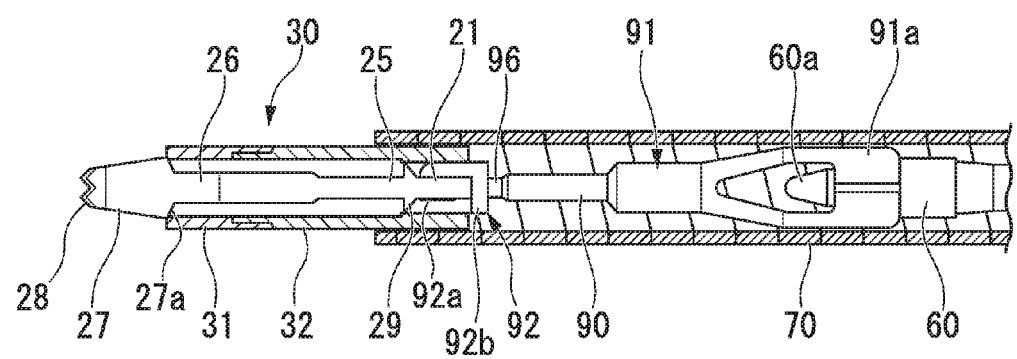
FIG. 8 is a partial sectional view showing the distal end portion of the endoscopic treatment instrument according to the first embodiment of the present invention.

In the initial state, when the operation wire 60 is pulled to the proximal end side, the bending portion 21 of the clip main body 20 moves to a position more proximal than the third insertion lumen 35. As shown in FIGS. 7 and 8, when the first extension portion 23 and the second extension portion 24 are disposed in the third insertion lumen 35, the outer surface of the first arm 22 is pressed such that the fourth portion 28 of the first arm 22 is pulled to the proximal end side while being elastically deformed so as to approach the distal end portion 41 of the second arm 40.

Next, with regard to an operation of the treatment instrument 1 when the ligation treatment is performed, an example of ligating a mucous membrane T inside a gastrointestinal tract will be described with reference to FIGS. 1 to 11.

First, the endoscope insertion portion is inserted into the vicinity of a treatment target area inside the gastrointestinal tract. Subsequently, an operator presses the treatment instrument 1 in a state shown in FIG. 5A so as to protrude the treatment instrument 1 from the distal end of the endoscope insertion portion. Furthermore, as shown in FIG. 5B, when the clip unit 10 is pressed so as to protrude from the distal end of the sheath 70, the protruding portion 32c engages with the distal end of the sheath 70 such that a movement of the pressing tube 30 with respect to the sheath 70 in the proximal end direction of the longitudinal axis L is restricted.

Next, when the slider 81 of the operation unit 80 is operated to slide to the distal end side, the operation wire 60 moves relative to the distal end side with respect to the sheath 70, and the coupling member 90 is pressed to the distal end side. When the coupling member 90 is pressed to the distal end side, the clip main body 20 moves to the distal end side inside the pressing tube 30. The second portion 26 of the first arm 22 protrudes from the distal end of the first tubular portion 31, the pressing force applied to the first arm 22 by the first tubular portion 31 is released such that the bent shape of the first arm 22 is restored, and the distal end portion of the first arm 22 moves in a direction spaced from the longitudinal axis L. At this time, the distal end of the first arm 22 is spaced from the distal end portion 41 of the second arm 40 in the direction inclining with respect to the longitudinal axis L.

Figure 9:
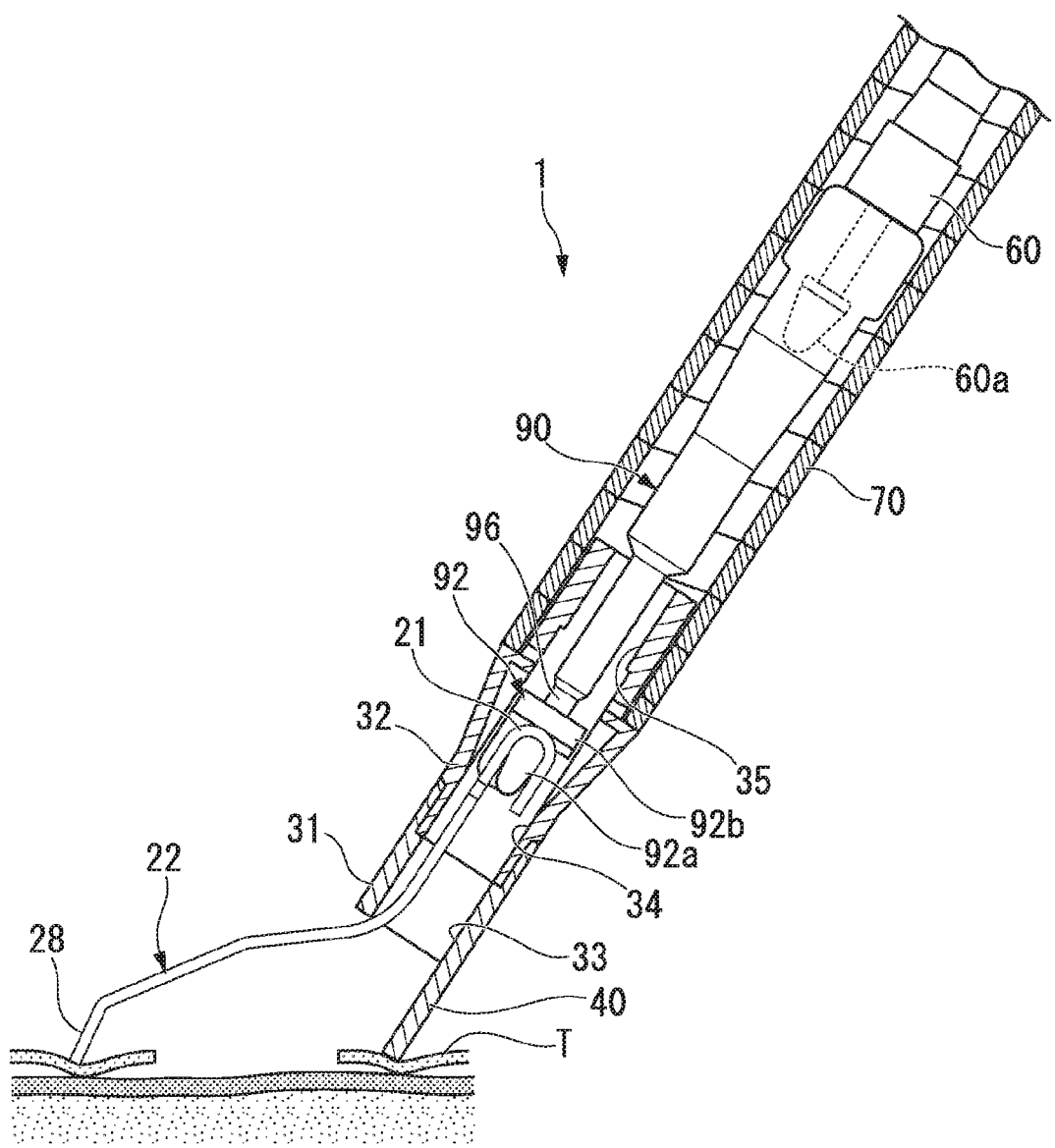
FIG. 9 is a view showing a use mode of the endoscopic treatment instrument according to the first embodiment of the present invention.

After a state where the first arm 22 and the second arm 40 are spaced from each other, the operator advances the sheath 70 with respect to the endoscope to cause the distal end portion 41 of the second arm 40 to press against the mucous membrane T in the vicinity of the ligation area. At this time, the endoscope insertion portion is present inside the gastrointestinal tract, and the ligation area is the mucous membrane T of the gastrointestinal tract. Accordingly, the treatment instrument 1 approaches the mucous membrane T in the direction inclining with respect to the mucous membrane T. The first arm 22 is located at a spaced position more distal than the distal end portion 41 of the second arm 40 such that when the distal end portion 41 of the second arm 40 is pressed against the mucous membrane T in the inclining direction, the distal end portion of the first arm 22 also comes into contact with the mucous membrane T, as shown in FIG. 9.

Figure 10:
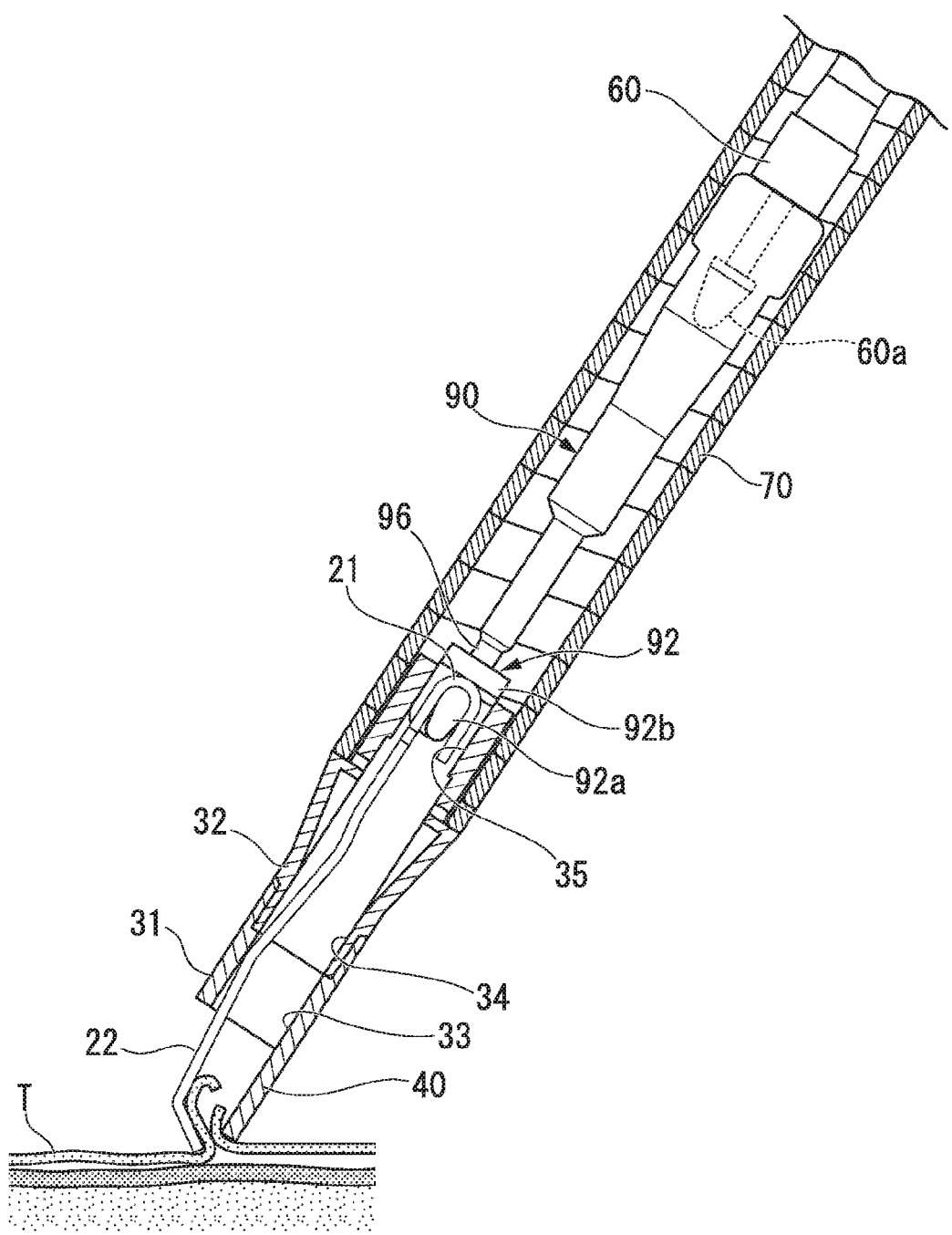
FIG. 10 is a view showing a use mode of the endoscopic treatment instrument according to the first embodiment of the present invention.

Subsequently, as shown in FIG. 10, the operator presses the treatment instrument 1 into the distal end side and pulls the slider 81 of the operation unit 80 to the proximal end side to pull the clip main body 20 to the proximal end side, in a state where the first arm 22 and the distal end portion 41 of the second arm 40 are pressed against the mucous membrane T. The slider 81 is pulled, and the bending portion 21 of the clip main body 20 is moved by the operation wire 60 to a position more proximal than the third insertion lumen 35. Furthermore, when the first extension portion 23 and the second extension portion 24 are disposed inside the third insertion lumen 35, the fourth portion 28 (distal end portion of the first arm) moves in a trajectory in the direction inclining with respect to the proximal end side so as to approach the distal end portion 41 of the second arm 40, and the fourth portion 28 approaches the distal end portion 41 of the second arm 40 to enter a closed state. The mucous membrane T to be ligated is grasped between the distal end portion of the first arm 22 and the distal end portion 41 of the second arm 40, and the first arm 22 and the second arm 40 function as a grasping portion 50 of the mucous membrane T.

The plate width of the third portion 27 is wider than the plate width of the second portion 26, and is larger than the opening width of the first tubular portion 31. Accordingly, when the second portion 26 is accommodated at a predetermined position inside the first insertion lumen 33, the proximal end portion 27a of the third portion 27 comes into contact with the distal end portion of the first tubular portion 31, thereby restricting the clip main body 20 from furtherly moving to the proximal end side. The operator recognizes that the clip main body 20 is accommodated at the predetermined position inside the pressing tube 30.

When the clip main body 20 is pulled to the proximal end side inside the third insertion lumen 35 through the first insertion lumen 33 and the second insertion lumen 34, the clip main body 20 is pulled to the proximal end side while being elastically deformed such that that the fourth portion 28 of the first arm 22 approaches the distal end portion 41 of the second arm 40 since the outer surface of the first arm 22 is pressed. When the bending portion 21, the first extension portion 23, and the second extension portion 24 come into contact with the third insertion lumen 35, the clip is brought into pressurizing contact with the pressing tube 30, and a state where the clip main body 20 is connected to the operation wire 60 via the coupling member 90 is maintained. Accordingly, a position of the pressing tube 30 is held in a state where the proximal end portion of the pressing tube 30 is inserted into the lumen of the sheath 70 and the protruding portion is in contact with the distal end surface of the sheath 70.

In a case where the mucous membrane T cannot be sufficiently grasped, the operation wire 60 is pressed outward to the distal side to restore the bent shape of the first arm 22, and the distal end portion of the first arm 22 moves in the direction spaced from the longitudinal axis L. In this manner, in a state where the first arm 22 and the second arm 40 are spaced from each other again, the mucous membrane T can be grasped again.

When the bending portion (connection portion) 21 is pulled to a position protruding from the proximal end of the pressing tube 30 such that the first arm 22 approaches the second arm to close the arm, the projection 29 is pressed into the third insertion lumen 35. The projection 29 has the above-described serrated shape, and thus, is brought into pressurizing contact with the inner wall of the third insertion lumen 35. The clip main body 20 is movable in the direction in which the clip main body 20 is pressed into the proximal end side (arm closing direction of the first arm 22), however, a movement of the clip main body 20 in a direction in which the clip main body 20 is pressed to the distal end side (direction in which the clip main body 20 protrudes from the pressing tube 30 so as to open the arm of the first arm 22) is restricted, as the projection 29 bites in the inner wall of the third insertion lumen 35.

Figure 11:
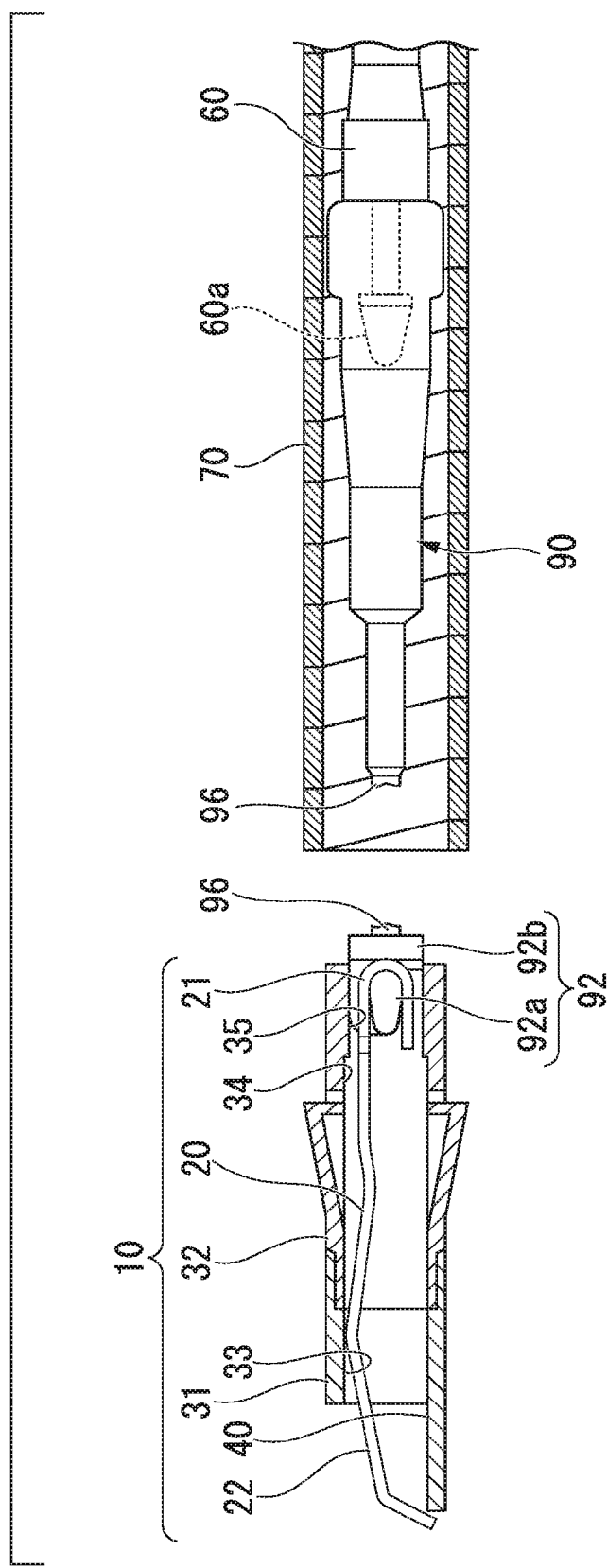
FIG. 11 is a view showing a use mode of the endoscopic treatment instrument according to the first embodiment of the present invention.

When the operation wire 60 is further pulled in a state where the first arm 22 and the second arm 40 grasp the mucous membrane T, the clip main body 20 does not move since the movement to the proximal end side is restricted by the engagement between the third portion 27 and the first tubular portion 31. Therefore, a heavy load is applied to the small diameter portion 96, thereby breaking the small diameter portion 96. In this manner, a connection between the operation wire 60 and the clip main body 20 is released. When the connection between the operation wire 60 and the clip main body 20 is released, a connection between the second tubular portion 32 and the distal end of the sheath 70 is also released, and as shown in FIG. 11, the pressing tube 30 is detached from the sheath 70, thereby placing the clip unit 10 after ligating the mucous membrane T. Thereafter, the sheath 70, the operation wire 60, and the proximal end side of the coupling member 90 are retracted from the endoscope insertion portion, thereby removing the treatment instrument 1 therefrom.

According to the treatment instrument 1 of the present embodiment, the grasping portion is configured to include the second arm 40 fixed to the pressing tube 30 and the first arm 22 of the clip main body 20 disposed to be advanceable and retractable with respect to the pressing tube 30. Therefore, the second arm 40 does not move even when the first arm 22 is pulled to the proximal end side of the pressing tube 30 in order to grasp a tissue. As a result, the second arm 40 can be stably pressed against the tissue without receiving the influence of the pulling operation performed by the operation wire 60 on the clip main body 20.

According to the treatment instrument 1 of the present embodiment, in the initial state, the position of the fourth portion in the direction of the longitudinal axis L of the pressing tube 30 is located on the distal end side from the position of the distal end portion 41 of the second arm 40. Accordingly, in a case where the treatment instrument 1 performs ligation by moving the clip unit 10 close to the ligation area in the oblique direction, both the distal end portions of the first arm 22 and the second arm 40 can be brought into a state where both of these are in contact with the tissue. In a case where the treatment instrument 1 transendoscopically ligates the mucous membrane T of the gastrointestinal tract, it is possible to smoothly perform the ligation process by pinching the mucous membrane T between the first arm 22 and the second arm 40.

A relative position of the second arm 40 with respect to the tissue can be fixed, and the second arm may not follow an operation in which the clip main body 20 is pulled in order to close the first arm 22. Accordingly, compared to the clip unit 10 in the related art, it is easy to perform the operation for pulling the clip unit 10 to the proximal end side while the clip unit 10 is pressed against the tissue.

The aspect according to the present embodiment is not limited to the above-described configurations. As a configuration of each unit, it is conceivable to adopt the following modification examples. Even if the modification examples are appropriately combined with each other, the tissue can be smoothly ligated similarly to the above-described embodiment. In the following description, the same reference numerals will be given to configurations common to the above-described configurations, and description thereof will be omitted.

Figure 12:
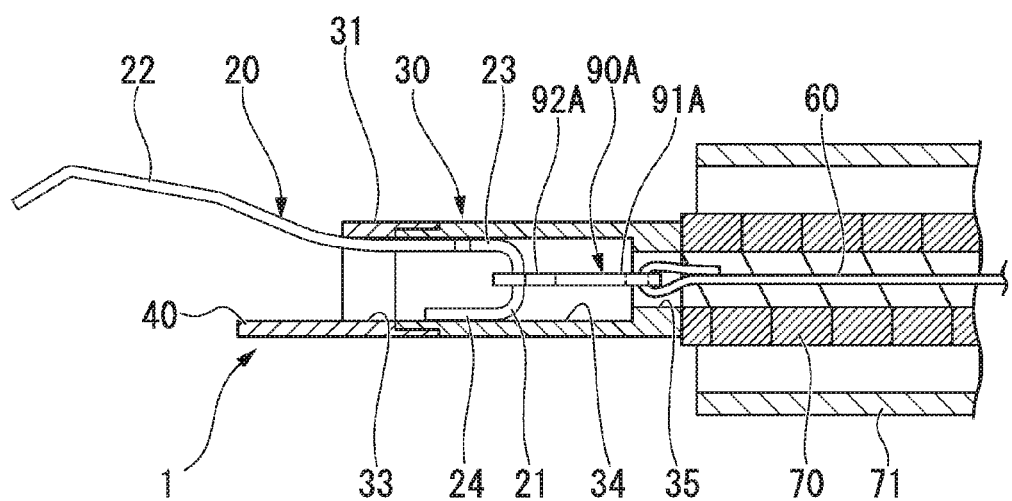
FIG. 12 is a partial sectional view showing a modification example of the endoscopic treatment instrument according to the first embodiment of the present invention.
Figure 13:
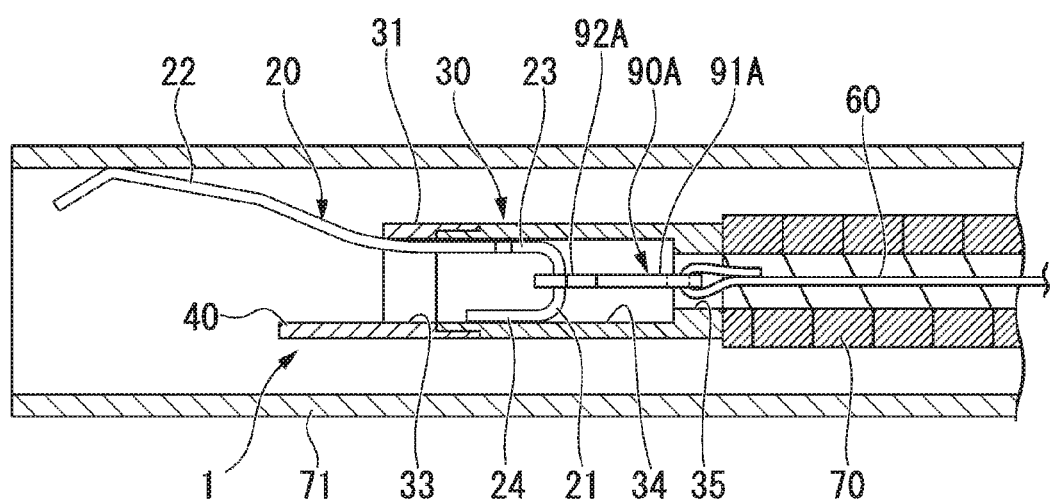
FIG. 13 is a partial sectional view showing a modification example of the endoscopic treatment instrument according to the first embodiment of the present invention.

In a case where the protruding portion 32C is not provided in the pressing tube 30, as shown in FIG. 12, a configuration may be adopted in which the movement of the pressing tube 30 is restricted by the proximal end of the pressing tube 30 coming into contact with the distal end of the sheath 70. In this case, the clip unit 10 in an accommodated state in an outer sheath 71 is inserted into the endoscope, and is caused to protrude from the distal end of the endoscope insertion portion. Thereafter, as shown in FIG. 13, the clip unit 10 is caused to protrude from the outer sheath 71 and used.

Modification Example of Clip Main Body

Figure 14:
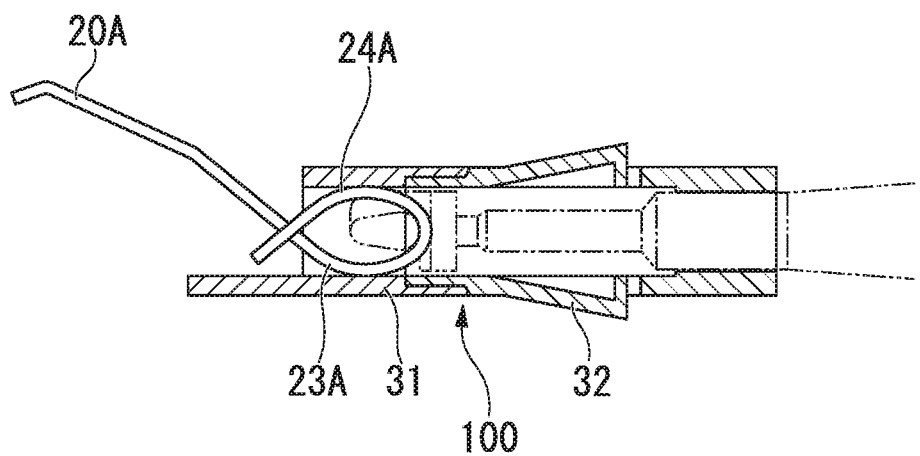
FIG. 14 is a sectional view showing a modification example of a clip main body according to the first embodiment.

In the present embodiment, a configuration has been described in which the first extension portion 23 and the second extension portion 24 extend from both ends of the bending portion 21 so as to be substantially parallel to each other. However, as shown in FIG. 14, a first extension portion 23A and a second extension portion 24A which extend from both end portions of the bending portion 21 may be formed in an a-shape in which both of these intersect each other. Alternatively, the first extension portion and the second extension portion may be formed in a tapered shape in which the spaced distance therebetween gradually becomes farther from both ends of the bending portion.

In the clip main body 20 according to the present embodiment, an example has been described in which the projection 29 is disposed so that the projection 29 functions as a wedge inside the third insertion lumen 35 and the clip main body 20 is fixed to the pressing tube 30, however, the projection 29 is not an essential configuration. For example, a configuration may be adopted in which the clip main body is fixed to the pressing tube by adjusting the dimension of the bending portion and the third insertion lumen so as to bring the bending portion and the third insertion lumen into pressurizing contact with each other.

First Modification Example of Second Arm

Figure 15:
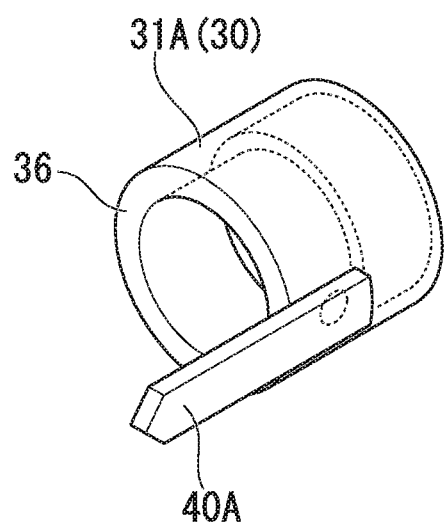
FIG. 15 is a perspective view showing a first modification example of a second arm according to the first embodiment.

In the present embodiment, an example has been described in which the second arm 40 is integrally molded with the second tubular portion 32, however, the second arm may be fixed in a state where the second arm protrudes from the distal end of the pressing tube 30. For example, as shown in FIG. 15, a configuration may be adopted in which a second arm 40A is fixed to an outer peripheral surface of a first tubular portion 31A (pressing tube) by means of welding or by using an adhesive.

Second Modification Example of Second Arm

Figure 16:
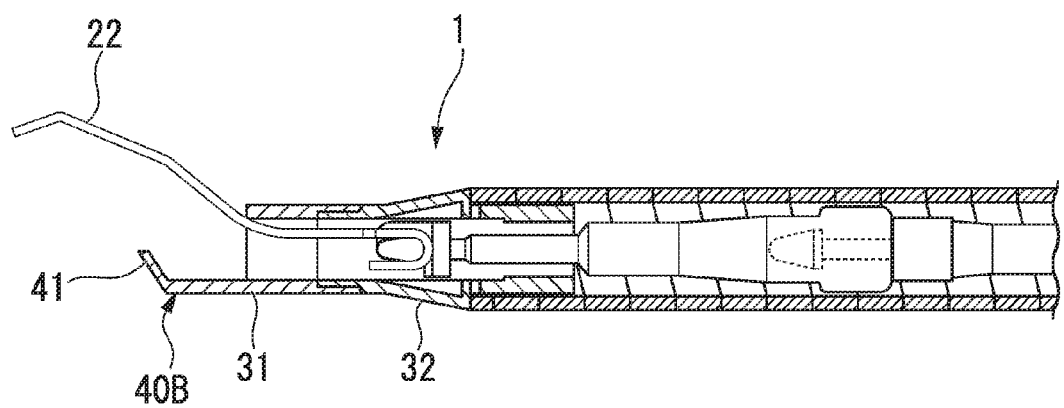
FIG. 16 is a partial sectional view showing a second modification example of the second arm according to the first embodiment.
Figure 17:
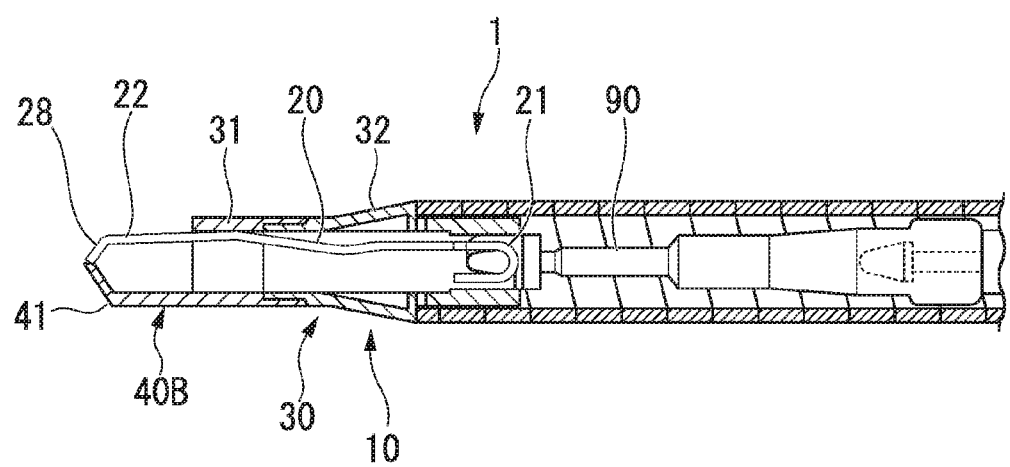
FIG. 17 is a partial sectional view showing the second modification example of the second arm according to the first embodiment.

In the present embodiment, an example has been described in which the distal end portion 41 of the second arm 40 linearly extends from the first tubular portion 31, however, a configuration may be adopted in which the second arm faces the first arm so as to be capable of grasping the tissue. For example, as shown in FIGS. 16 and 17, a claw portion may be employed in which the distal end portion 41 of a second arm 40B is folded in a direction close to the longitudinal axis L of the first tubular portion 31. In this case, as shown in FIG. 17, in a closed state of the clip main body 20, the fourth portion 28 (distal end of the first arm) of the first arm 22 and a claw portion 41 (distal end portion of the second arm) face each other, thereby enabling the tissue to be more firmly grasped. Furthermore, if the fourth portion 28 (distal end of the first arm) of the first arm 22 and the claw portion 41 (distal end portion of the second arm) are configured to face each other on the longitudinal axis L, the tissue can be much more firmly grasped.

Third Modification Example of Second Arm

Figure 18:
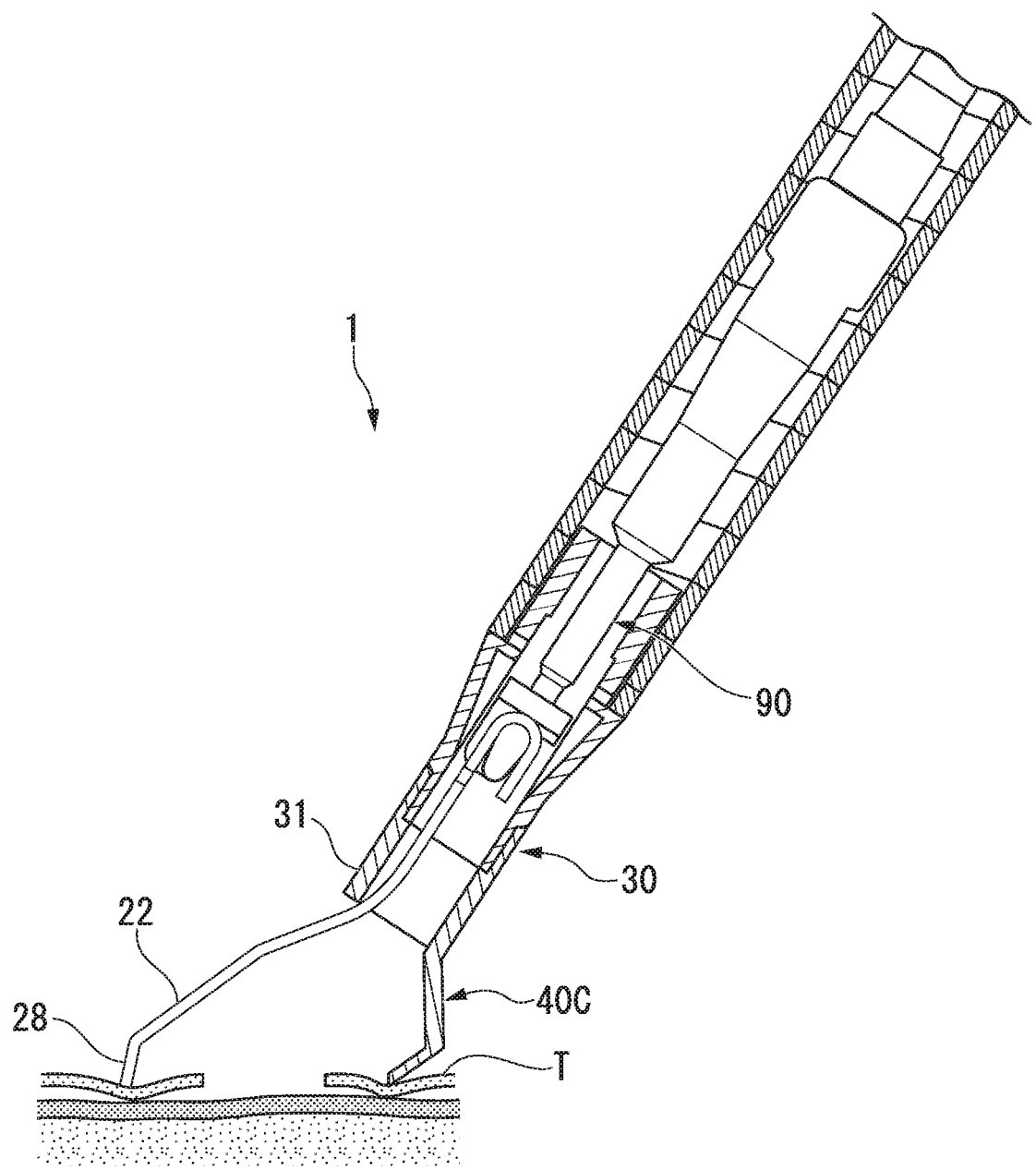
FIG. 18 is a view showing a use mode according to a third modification example of the first embodiment.
Figure 19:
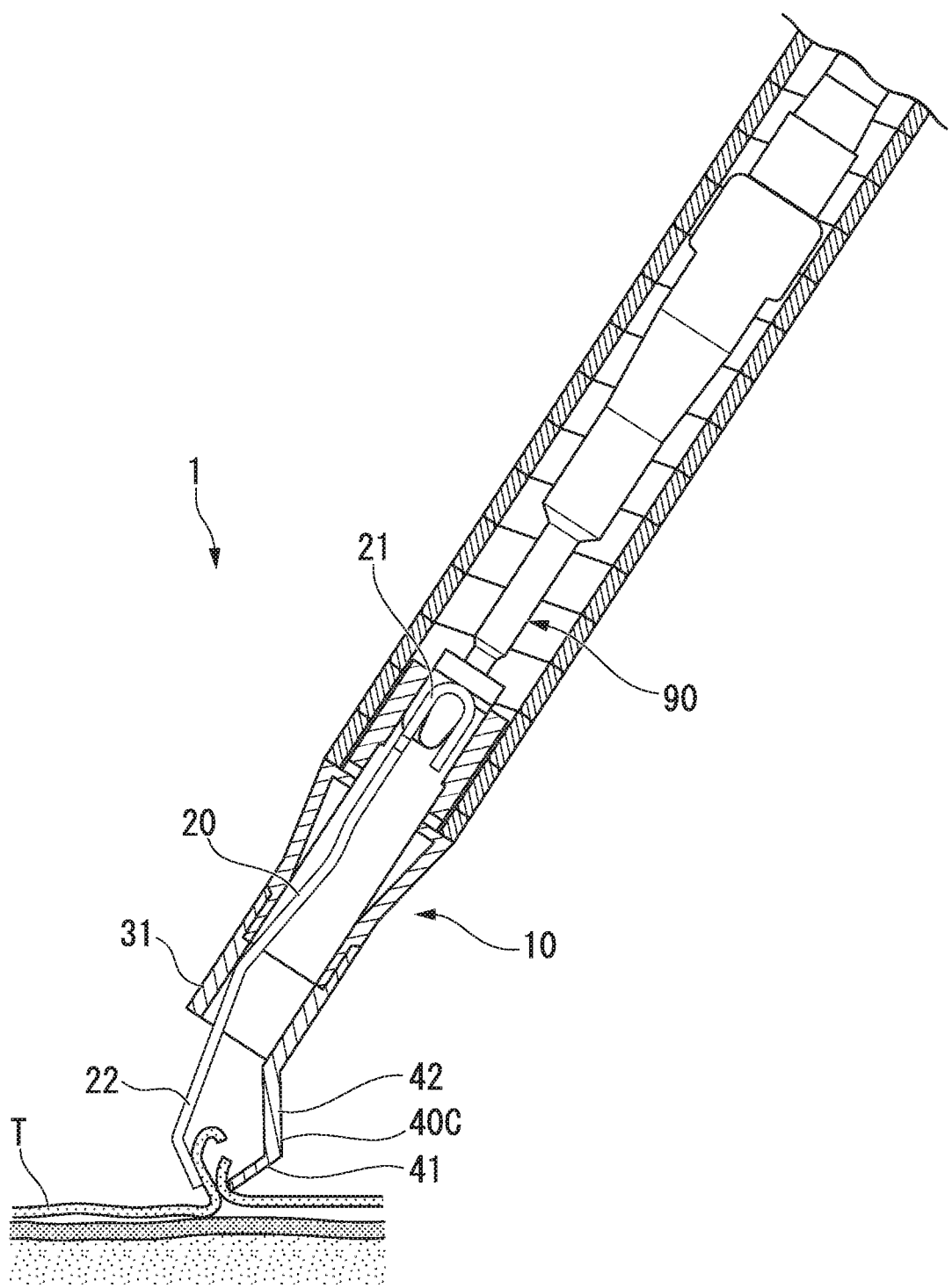
FIG. 19 is a view showing a use mode according to the third modification example of the first embodiment.

A second arm 40C may be formed of a material or in a shape which has rigidness such that an extent that the proximal end portion 42 can be bent by an external force. That is, in a state where the external force is not applied to the second arm 40C, as in the second modification example shown in FIGS. 16 and 17, the proximal end portion of the second arm 40B linearly extends on an extension line of the first tubular portion 31. On the other hand, if the external force is applied thereto when the tissue is pressed, as shown in FIGS. 18 and 19, the second arm 40C is rigid to such an extent that the proximal end portion is bent in the direction spaced from the longitudinal axis L of the first tubular portion 31. In this way, the proximal end portion of the second arm 40C is bent, and thus, it is possible to stably hold a position where the distal end of the second arm 40C comes into contact with the tissue. As a result, even if an angle at which the pressing force is applied to the tissue by the treatment instrument 1 is changed during the operation, it is possible to stably hold a state where the second arm 40C presses the tissue in the pressing direction. When the second arm 40C presses the tissue, it is possible to prevent the second arm 40C from sliding on and slipping off from the tissue.

Modification Example of Pressing Tube

An example has been described in which the first tubular portion 31 and the second tubular portion 32 are joined to each other in the pressing tube 30, however, without being limited thereto, a configuration may be adopted in which the first tubular portion 31 and the second tubular portion 32 are integrally molded.

For example, an opening shape of the insertion lumens (the first insertion lumen, the second insertion lumen, and the third insertion lumen) of the pressing tube may be a circular shape, an elliptical shape, an oval shape, or a rectangular shape, as long as the shape enables the clip main body and the coupling member to move forward or rearward.

First Modification Example of Coupling Member

The coupling member 90 may be configured so that the coupling member 90 is coupled to the distal end of the operation wire 60, and so that the clip main body 20 and the operation wire 60 are coupled so as to be detachable from each other. For example, the coupling member 90A according to the first modification example shown in FIGS. 12 and 13 has a coupler 91A formed from a flat plate which is long in the axial direction of the operation wire 60. The coupler 91A has a through-hole formed to penetrate the proximal end portion of the coupling member 90A in the thickness direction, and has an opening area into which the operation wire 60 can be inserted. The distal end of the operation wire 60 is inserted into the opening of the coupler 91A of the coupling member 90A. Thereafter, the distal end returns to the proximal end side so as to form a loop, and is fixed to the operation wire 60, thereby coupling the coupling member 90A and the operation wire 60 to each other. The distal end side of the coupling member 90A has a hook-shaped engaging portion 92A. The bending portion 21 of the clip main body 20 is disposed in the hook-shaped portion of the engaging portion 92A, thereby adopting a configuration in which the clip main body 20 can be engaged.

The coupling member 90A is configured to be advanceable and retractable in the second insertion lumen 34, in the third insertion lumen 35 of the pressing tube 30 fixed to the distal end of the sheath 70, and in the lumen of the distal end portion of the sheath 70 due to a relative movement of the operation wire 60 with respect to the sheath 70 by the operation of the operation unit 80.

Alternatively, for example, as another connection structure between the coupling member and the operation wire 60, a structure may be employed in which the coupling member is fixed to the distal end of the operation wire 60 by means of welding.

Second Modification Example of Coupling Member

Figure 20:
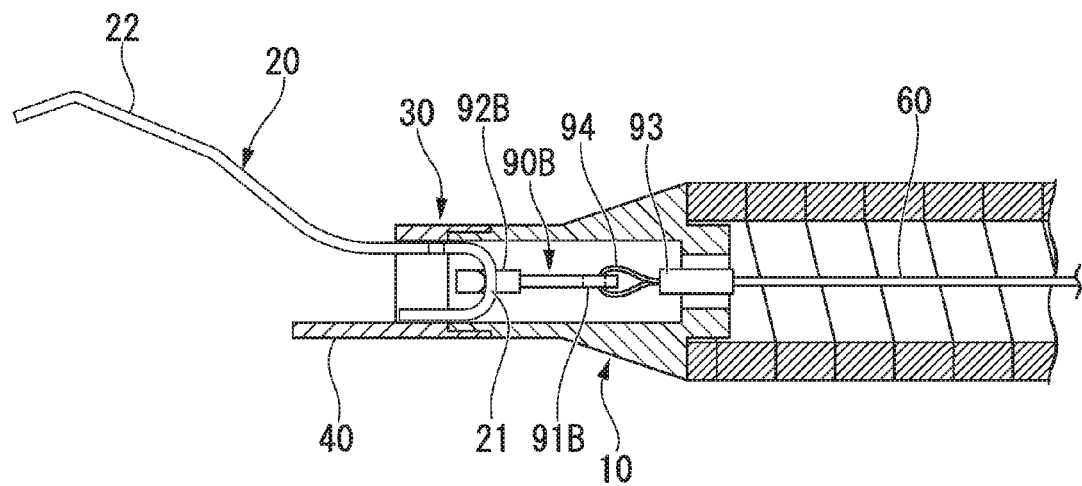
FIG. 20 is a partial sectional view showing a second modification example of a coupling member according to the first embodiment.
Figure 21:
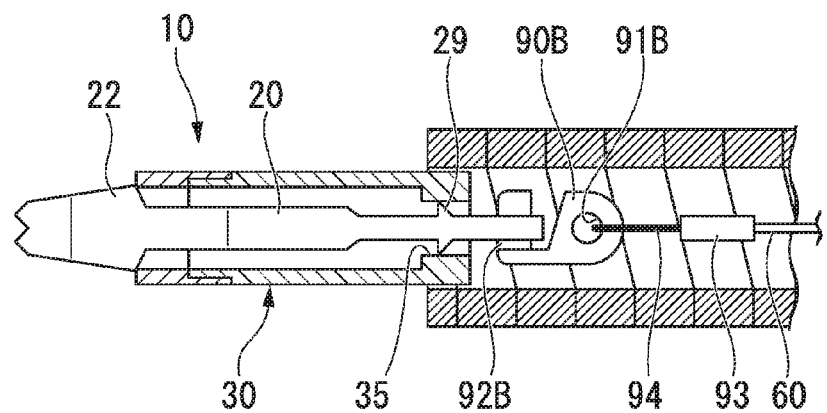
FIG. 21 is a partial sectional view showing the second modification example of the coupling member according to the first embodiment.

A second modification example of the coupling member is shown in FIGS. 20 and 21. In a coupling member 90B according to the second modification example, an engaging portion 92B is formed in a hook shape which is cut out inward in a rectangular shape from a portion of the outer peripheral edge extending in the direction of the longitudinal axis L. The distal end of the operation wire 60 is fixed to a proximal end member 93 of the coupling member 90B. A loop wire 94 disposed on the distal end side of the proximal end member 93 is inserted into a coupler 91B formed from a through-hole.

Figure 22:
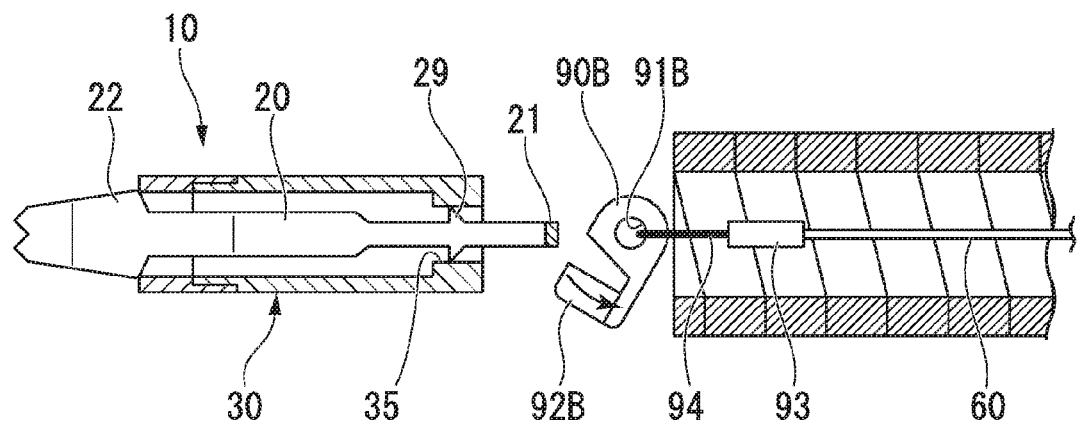
FIG. 22 is a partial sectional view showing the second modification example of the coupling member according to the first embodiment.

According to the coupling member 90B of the present modification example, as shown in FIG. 21, in a state where the clip main body 20 is pulled such that the bending portion 21 is disposed more proximal than the second tubular portion 32 and the clip main body 20 is fixed to the pressing tube 30 by the third insertion lumen 35 and the projection 29, the coupling member 90B cannot pivotally move inside the sheath 70 in the outer circumferential direction of the sheath. Accordingly, the engagement between the engaging portion 92B and the clip main body 20 cannot be released in this state. On the other hand, as shown in FIG. 22, when the operator moves the operation wire 60 toward the distal end side of the sheath 70, the coupling member 90B can pivotally move in the outer circumferential direction of the sheath 70 such that the engagement between the engaging portion 92B and the clip main body 20 can be released.

Third Modification Example of Coupling Member

Figure 23:
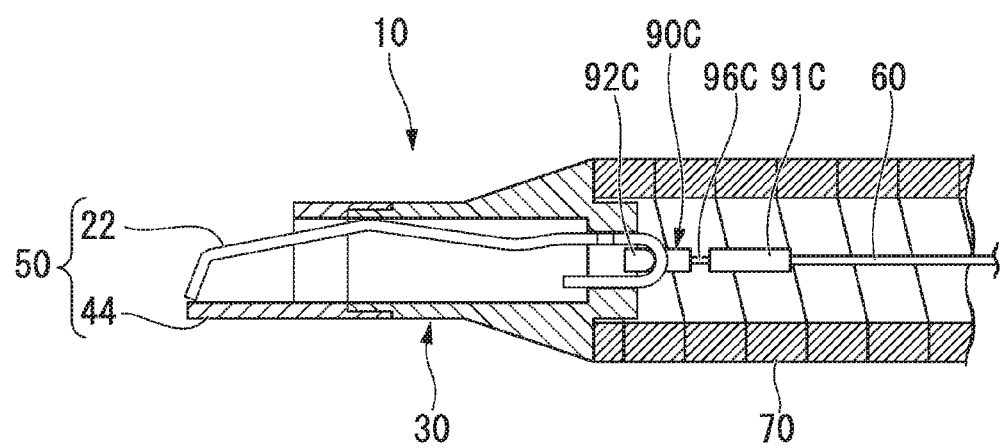
FIG. 23 is a partial sectional view showing a third modification example of the coupling member according to the first embodiment.

FIG. 23 shows a third modification example of the coupling member. A coupling member 90C according to the third modification example has a small diameter portion 96C between a connection portion side of the operation wire 60 and the coupling member 90C and an engaging portion 92C side. The small diameter portion 96C is set to have weaker tensile strength than that of other portions of the coupling member 90C, and is configured so that strong tension is applied to the coupling member 90C and the small diameter portion 96C is broken. According to the coupling member 90C of the present modification example, in a state where the clip main body 20 is pulled such that the bending portion 21 is disposed more proximal than the second tubular portion 32 and the clip main body 20 is fixed to the pressing tube 30 by the third insertion lumen 35 and the projection 29, when the operator further pulls the operation wire 60, the small diameter portion 96C is broken and the connection of the clip main body 20 and the operation wire 60 is released as the clip main body 20 does not move.

In the present modification example, an example has been described in which the small diameter portion 96C is broken so as to release the connection between the clip unit 10 and the operation wire 60, however, a configuration may be adopted in which a hooked shape of the engaging portion 92C is broken or plastically deformed so as to release the connection between the clip main body 20 and the operation wire 60.

Alternatively, an example has been described in which the treatment instrument 1 grasps the tissue by using the first arm 22 and the second arm 40, however, a configuration may be adopted in which the treatment instrument 1 has an arm fixed to the pressing tube and an arm disposed so as to be advanceable or retractable with respect to the pressing tube so as to grasp the tissue by using these arms. For example, a configuration may be adopted in which two second arms are disposed for the pressing tube so that the first arm grasps the tissue by facing each of the two second arms, or a configuration may be adopted in which a plurality of first arms and second arms are caused to face each other so as to grasp the tissue.

Hitherto, the embodiments according to the present invention have been described with reference to the drawings. However, a specific configuration is not limited to the embodiments, and includes design modifications within the scope not departing from the gist of the present invention.

In addition, a configuration can be adopted by appropriately combining the configuration elements described in the respective embodiments and the respective modification examples with each other. The present invention is not limited by the above description, and is limited by only appended claims.

What is claimed is:

1. An endoscopic treatment instrument, comprising:
    a pressing tube that has an insertion lumen;
    a clip main body that has a first arm, the first arm being inserted into the insertion lumen such that the first arm protrudes from a distal end portion of the pressing tube;
    a second arm that is fixed to the pressing tube to protrude to a distal end side of the pressing tube; and
    an operation wire that is connected to the clip main body and configured to advance and retract the clip main body with respect to the pressing tube,
    wherein the first arm approaches the second arm while being moved to a proximal end side of the pressing tube by being pulled by the operation wire,
    wherein in an initial state before the clip main body is pulled by the operation wire, a position of a distal end portion of the first arm in a longitudinal axis direction of the pressing tube is more distal than a position of a distal end portion of the second arm, and
    wherein the distal end of the first arm is configured to approach the distal end portion of the second arm when the clip main body is pulled to the proximal end side of the pressing tube.

2. The endoscopic treatment instrument according to claim 1,
    wherein the first arm is disposed so as to incline with respect to a longitudinal axis of the pressing tube when the first arm protrudes from the distal end portion of the pressing tube, and
    wherein the second arm is fixed to the pressing tube at an angle which is substantially parallel to the longitudinal axis.

3. The endoscopic treatment instrument according to claim 2,
    wherein the clip main body has a connection portion to be connected to the operation wire on the proximal end side of the clip main body, and
    wherein a connection between the operation wire and the clip main body is released as the connection portion protrudes from the proximal end of the pressing tube, while the clip main body is pulled toward the proximal end side of the pressing tube.

4. The endoscopic treatment instrument according to claim 1,
    wherein the first arm is configured to be elastically deformable and have a shape inclined in a direction in which the distal end portion of the first arm is spaced from the longitudinal axis of the pressing tube, in a state where the first arm protrudes from the distal end portion of the pressing tube, and wherein the first arm is pressed by the pressing tube to be elastically deformed when the clip main body is pulled to the proximal end side of the pressing tube.

* * * * *